United States Patent [19]

Herwig et al.

[11] Patent Number: 4,712,434
[45] Date of Patent: Dec. 15, 1987

[54] DEVICE FOR EMISSION-FREE SAMPLING OF VOLATILE LIQUIDS

[75] Inventors: Jens Herwig, Cologne; Hagen Nörenberg, Dormagen; Friedhelm Bergmann, Cologne; Manfred Stiller, Dormagen; Horst Schlemmermeyer; Wilfried Schmidt, both of Cologne; Hilmar Straube, Pulheim; Helmut Wolter, Cologne, all of Fed. Rep. of Germany

[73] Assignee: EC Erdölchemie GmbH, Koeln-Worringen, Fed. Rep. of Germany

[21] Appl. No.: 914,104

[22] Filed: Oct. 1, 1986

[30] Foreign Application Priority Data

Oct. 25, 1985 [DE] Fed. Rep. of Germany ....... 3537940

[51] Int. Cl.$^4$ ............................................. G01N 1/10
[52] U.S. Cl. ................... 73/864.63; 73/863.71
[58] Field of Search ........... 73/863.71, 863.72, 863.73, 73/863.83, 863.86, 864, 864.31, 864.33, 864.34, 864.91, 864.41, 864.51, 864.52, 863.81, 864.32, 863.31, 863.33, 863.03, 863.02, 863.01, 863, 863.57, 863.58, 863.85, 864.63

[56] References Cited

U.S. PATENT DOCUMENTS

| | | | |
|---|---|---|---|
| 2,245,679 | 6/1971 | Kelley | 73/863.81 |
| 3,083,577 | 4/1963 | Nelson et al. | 73/863.71 |
| 3,504,549 | 4/1970 | Davis et al. | 73/863.71 |
| 3,798,972 | 3/1974 | Collins, Jr. | 73/863.71 |
| 3,973,440 | 8/1976 | Vande Ven et al. | 73/863.81 |
| 4,194,398 | 3/1980 | Gastrock | 73/863.71 |
| 4,628,749 | 12/1986 | Rafter, Jr. | 73/863.71 |

FOREIGN PATENT DOCUMENTS 0614357 7/1978 U.S.S.R. ........................... 73/863.58

Primary Examiner—Stewart J. Levy
Assistant Examiner—Robert R. Raevis
Attorney, Agent, or Firm—Sprung Horn Kramer & Woods

[57] ABSTRACT

A device for emission-free sampling of volatile liquids comprises a 4-way tap from which lead two lines, which can be connected together, from and to the container holding the liquid to be tested and two other lines, which can also be connected together, lead to a sample bottle which can be sealed and which can be connected to the device. The device further comprises a supply line for an inert flushing medium, which joins the line leading into the sample bottle in the region of the sample bottle, and a discharge line for the inert flushing medium, which leads from the line coming out of the sample bottle in the region of the sample bottle and proceeds to a disposal system.

10 Claims, 1 Drawing Figure

DEVICE FOR EMISSION-FREE SAMPLING OF VOLATILE LIQUIDS

BACKGROUND OF THE INVENTION

The present invention relates to a device for sampling volatile liquids without emissions of the volatile liquid to be investigated occurring during the sampling. For this purpose, the device has, in addition to the facility for the actual sampling, additional facilities for flushing the sampling device according to the invention with an inert flushing medium, with the used flushing medium and residual quantities of the volatile liquid to be investigated being passed to a disposal system.

For the reasons of work hygiene, environmental protection and safety, especially in chemical or petrochemical plants, it is necessary to sample volatile liquids to be investigated in an emission-free manner. The following requirements, amongst others, are made for a device for emission-free sampling:

1. The sample should be representative of the volatile liquid present at the sampling point. This generally means that the sample, which is to be removed from a container, pipeline or plant part, flows for a certain time, a few minutes for example, before the desired sample is taken in order to prevent liquid remaining in so-called "dead corners" or pipe ends, which are possibly changed, from being transferred to the sample container.

2. Emissions at the sampling point should be avoided so that it is possible to dispense with heavy protective equipment, such as heavy respirators, when dealing with substances which are dangerous in a work environment. Furthermore, contamination of the sample taken should be avoided. Both points require that the sampling device be flushed, and the flushing medium must be disposed of in a suitable fashion.

3. Operating errors with undesirable consequences should be excluded as much as possible.

4. The installation and handling of the sampling device should be possible with acceptable expenditure.

5. The sample bottle should always be filled to the same desired degree, in particular, the sample bottle should have a gas cushion above the volatile liquid to be tested in order to avoid bursting of the sample bottle during temperature variations.

SUMMARY OF THE INVENTION

The requirements mentioned are fulfilled by the device, according to the invention, for emission-free sampling of volatile liquids which comprises a 4-way tap from which lead two lines, which can be connected together via the 4-way tap, from and to the container holding the liquid to be tested and from which the two other lines, which can also be connected together via the 4-way tap, lead to a sample bottle which can be sealed and which can be connected to the device, and which further comprises a supply line, for an inert flushing medium, which joins the line leading to the sample bottle in the region of the sample bottle, and a discharge line, for the inert flushing medium, which leaves the line coming from the sample bottle in the region of the sample bottle and leads to a disposal system.

BRIEF DESCRIPTION OF THE DRAWINGS

The construction and mode of operation of the device according to the invention is explained below with the aid of the accompanying drawing, wherein the FIGURE is a schematic representation of the device according to the invention.

DETAILED DESCRIPTION OF THE INVENTION

Figure 1:
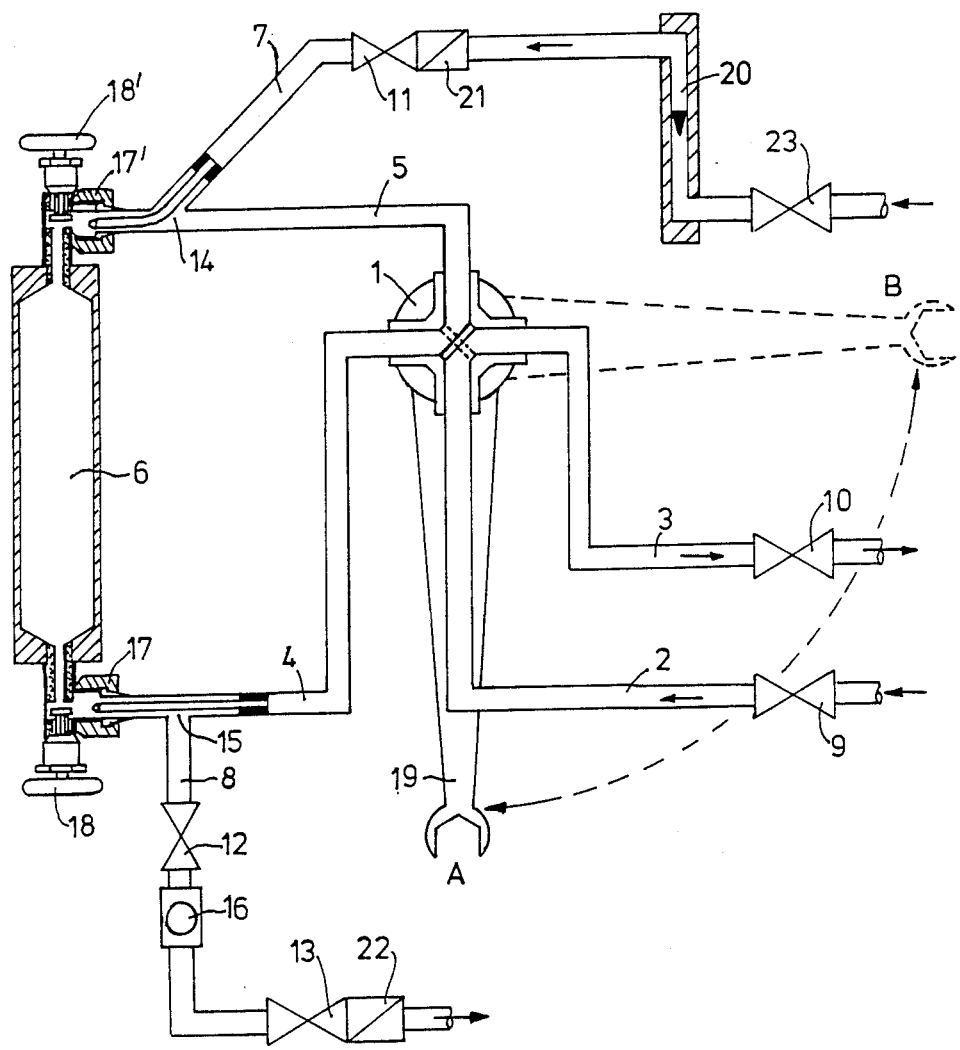

A 4-way tap 1 is installed on a suitable mounting frame, and is connected to the container holding the medium to be tested via a supply line 2 and return line 3 on two of its outlets. This container can be a storage container, a pipeline or any other plant part; 2 and 3 can, for example, be the pressure or vacuum side of a pump or a pipeline bypass. 2 and 3 are connected with 1 in such a way that the lines 2 and 3 are connected together when 1 is set to position A. A line 4 leads from 1 to the sample bottle 6 which can be connected to the device according to the invention. A further line 5 leads from 6 back to 1. 4 and 5 are also connected together when 1 is set to position A.

The sample bottle 6 is connected to the ends of 4 and 5 in a suitable fashion, for example, by means of a sliding joint, a so-called bayonet joint or a screw joint, for example with union nuts. The screw joint with union nuts is a preferred form of the connection of 6, represented in the drawing by two union nuts 17 and 17'. The sample bottle 6 is sealed in a known manner, for example by means of screw valves 18 and 18'.

The lines 4 and 5 are fitted with a branch 14 and 15 in the region of the connection 17 and 17' of 6. This branch can be constructed as a T or Y piece, for example. At 14, the supply line 7 for an inert flushing medium leads into 5. At 15, a discharge line 8 for the inert flushing medium leaves 4; 8 leads to a disposal system where residual quantities of the volatile liquid which has been carried with the inert flushing medium are removed in a suitable fashion. This can be carried out, for example, by means of a washer, a flare system or by another combustion means. Return of excess volatile liquid with the flushing medium to a suitable point in the process is also possible as a disposal method to be aimed at.

Within the device according to the invention, 6 can be mounted basically in the horizontal position or in a position deviating from the horizontal. In a preferred embodiment, the position of 6 deviates from the horizontal so that 17' and 18', for example, lie higher than 17 and 18. This means that, at the same time, 5 and 7 also lie spatially higher than 4 and 8. In an especially preferred fashion, the device according to the invention is designated so that the sample bottle is connected in a vertical position.

In a further preferred embodiment, which is also shown in the FIGURE, the supply line 7 runs as a coaxial double pipe from before the entry 14 up to the immediate vicinity of the valve seat of 18'. This ensures that residual quantities of the sampled volatile liquid cannot remain in the "dead corner", for example, in the region of 17' and 18' during the flushing process. In an analogous fashion, the connection of 8 and 4 at 15 runs as a coaxial double pipe up to the valve seat of 18. Of course, the described double pipe does not have to be strictly coaxial for the mode of action represented. Furthermore, it is unimportant whether the joining line 7 or the line 5 forms the inner pipe of the mentioned double pipe. It is also unimportant whether 4 or 8 forms the inner pipe of the double pipe in the discharge line of the inert flushing medium 15. In a preferred fashions, the embodiment represented in the drawing is selected, in which the line 7 is constructed as the inner pipe at 14 and the line 4 is constructed as the inner pipe at 15.

In a further preferred embodiment of the device according to the invention, the discharge line 8 for the inert flushing medium is fitted with a double isolation by means of the taps or valves 12 and 13. An inspection glass 16 can be located between 12 and 13. In a particularly preferred form, the volume in the line 8 between 12 and 13 is identical with the gas volume which is above the liquid level and is meant to be reproducible. The liquid filling volume of 6 aimed at amounts, for example, to 60–95% of the total volume of 6. With the aid of this preferred embodiment of the device according to the invention, it is then possible, if 1 is in lever position A, line 7 is closed by means of the tap or the valve 11 and the sample bottle 6 is opened at both ends at 18 and 18', that the inert flushing gas retained between 12 and 13, after 12 is opened, pushes out of 6 and 5 such a part of the liquid taken as sample that the desired filling volume in 6 is achieved. For its part, the sample medium pushed out of 6 and 5 flows into the region between 12 and 13. Position A of 1 is characterized in that the volatile liquid intended for sampling can be guided in a circle via 2 and 3 as supply and return lines (small circuit).

In a preferred embodiment, the operating lever 19 of 1 is constructed as a spanner in a suitable size for screwing 17 and 17' of 6. In a particularly preferred embodiment, lever or wrench 19 is clamped in such a fashion that it can only be removed and thus used to unscrew 17 and 17' in position A.

The device according to the invention is, in principle, suitable for all liquids which can be displaced and vaporized by an inert gaseous flushing medium. These can be liquidized gases under pressure as well as substances and their mixtures which are liquid at normal pressure. The device according to the invention can, for this purpose, be constructed so as to be pressure-proof in a fashion familiar to the expert.

The device according to the invention is suitable in a particular fashion for aggressive, volatile liquids which are toxic, corrosive or environmentally dangerous in another way. If it is necessary for this purpose, the device according to the invention can be constructed so as to be corrosive-proof. Corrosive-proof material are, for example, corrosive-proof metals, such as stainless steel, semi-precious or precious metals, other corrosion-proof inorganic materials, such as glass or ceramics, or corrosion-proof organic materials, such as polyethylene or polypropylene. The use of such corrosion-proof materials for various corrosive substances is familiar to the expert.

Examples of volatile liquids are: inorganic substances, such as HF, HCL, HBr, $NH_3$, $HNO_3$ and others; organic substances, such as hydrocarbons with boiling points up to about 150° C., e.g. saturated or unsaturated aliphatic or aromatic hydrocarbons and their mixtures, fuels or fuel components; halohydrocarbons with a boiling point up to about 150° C., such as methylene chloride, chloroform, carbon tetrachloride, 1,1,1-trichloroethylene and others; acids, such as formic acid, acetic acid or prussic acid; various ethers, esters, ketones or alcohols; epoxides, such as ethylene oxide; and finally other hetero compounds, especially those which are toxic and difficult to handle, such as methyl isocyanate, phosgene, thionyl chloride and similar.

Examples of suitable inert gaseous flushing media are nitrogen and argon as well as their mixtures, and also, as long as no reaction with the sample medium is to be feared, also carbon dioxide, methane or others. In a preferred fashion, nitrogen, which is easily available, is used.

In principle, however, the device according to the invention can also be used for sampling substances which are volatilized with greater difficulty, and, especially, are toxic. In the flushing process, the substance which is volatilized with greater difficulty is first displaced with a low-boiling, volatile primary flushing medium and the primary flushing medium and the primary flushing medium is subsequently displaced from the device by one of the inert gaseous flushing media described above. Suitable primary flushing media can be, for example, tetrahydrofuran, acetone, methanol and others, which are used in such a fashion that no chemical reaction occurs between the liquid which is volatilized with greater difficulty and the primary flushing medium.

The pipelines in the device according to the invention are provided with suitable isolating members 9, 10, 11, 12, 13 and 23, such as taps or valves, which are known to the expert. The line 7 can, if appropriate, contain a measuring device, such as a rotameter 20 for the inert flushing medium. In addition, 7 and 8 can be fitted with safety devices, such as non-return valves 21 and 22.

Emission-free and safe sampling with the aid of the device according to the invention is represented by the following individual steps, referring to the accompanying drawings:

(a) The isolation devices 11, 12 and 13 are closed, the operating lever 19 holds the 4-way tap 1 in position A. As long as a sample bottle 6 is not yet connected, 19 is removed and a new sample bottle 6 screwed on at 17 and 17'. 19 is replaced on 1.

(b) To flush 6 and the complete device, 11, 12 and 13 are opened and filled with a suitable amount of inert flushing medium via 20. For this purpose, a suitable time, for example 3 minutes, is allotted. The flushing medium escapes via 13 and 22 to the disposal system. During the flushing process, the valves 18 and 18' of 6 are closed, if necessary, in order to flush 5, 1 and 4 as well.

(c) To start the product path (small circuit), 9 and 10 are opened and, if necessary, a pump of the plant part concerned from which the sample is to be taken is switched on. The liquid from which a sample is to be taken is passed through this small circuit (position A) for a suitable time, for example also 3 minutes. If it has not already been done in (a) above, the operating lever 19 is reset now at the latest.

(d) To end the flushing with the inert flushing medium, 11, 12 and 13 are closed.

(e) To fill 6 with the sample to be taken, 1 is set to position B using 19 and the large circuit is opened for an adequate period, for example again 3 minutes.

(f) To ensure that the aimed at degree of filling of 6 is achieved, 1 is reset to position A, the isolation 12 is opened and an adequate period allowed (for example a further 3 minutes) for the inert flushing medium, which has been retained between 12 and 13 until now, to pass into 5 and into the upper part of 6. During this, the level of the sample taken falls in 6 to the aimed at mark. As already described above, measuring accuracy is, in general, unnecessary during this since a gas cushion in the upper part of 6 serves mainly as a safety measure so that temperature fluctuations do not cause 6 to burst. It should be ensured that a specified safety gas cushion is reached.

(g) To empty and flush the sampling device according to the invention, 9 and 10 are first closed and, if necessary, cut off from the product pump. In addition, the sample bottle valve s 18 and 18' are closed. 11 and 13 are then opened, an adequate amount of flushing medium is admitted via 20 and the lines 5, 4 and 8, as well as the interjacent region of 1, are flushed for an adequate time (for example again 3 minutes).

If the flushing is carried out at increased inert gas pressure and the sampling system is still under an increased pressure before the sample bottle is unscrewed, it is recommended that an additional valve be installed in the region of lines 4 and 5 to ensure a calculated reduction of pressure.

(h) To remove the sample bottle 6, 11, 12 and 13 are closed, the lever 19 is removed and the joints 17 and 17' are unscrewed.

(i) The next sample bottle is, in general, attached now in order to secure the sampling system.

We claim:

1. A device for the emission-free sampling of volatile liquids, comprising: a 4-way tap having four lines and actuatable into two alternative states including a first state wherein a first and a second line are fluidly coupled and a third and a fourth line are fluidly coupled and a second state wherein the first and third lines are fluidly coupled and the second and fourth lines are fluidly coupled, wherein the first and second lines are fluidly connectable to a container holding the liquid to be tested, and the third and fourth lines are fluidly connectable to a sample bottle, a supply line for receiving an inert flushing medium and which is fluidly joined to the fourth line in a region of the connection to the sample bottle, and a discharge line for the inert flushing medium and which is branched from the third line in a region of the connection to the sample bottle and fluidly connectable to a disposal system and wherein the sample bottle has a longitudinal axis and is connected in a position in which the longitudinal axis deviates from the horizontal and the fourth line which terminates at the sample bottle and the supply line for the inert flushing medium lie at a higher level with respect to gravity than the third line coming from the sample bottle and higher than the discharge line for the inert flushing medium.

2. The device according to claim 1, wherein the sample bottle is connected with its longitudinal axis in a vertical position.

3. The device according to claim 1, wherein the supply and discharge lines for the inert flushing medium are physically joined by a T or Y piece, and comprise a coaxial double pipe up to the connection to the sample bottle.

4. The device according to claim 3, wherein the discharge line for the inert flushing medium is fitted with two spaced apart isolation elements, and an inspection glass located between the two isolation elements.

5. The device according to claim 4, wherein the volume enclosed by the double isolation is dimensioned such that when the 4-way tap is in the first state and the upstream isolation is opened, a predetermined filling of the sample bottle results.

6. The device according to claim 5, wherein the predetermined filling of the sample bottle is 60–95% of the total volume of the sample bottle.

7. The device according to claim 1, wherein the sample bottle is connected to each of the third and fourth lines by a screw joint and the 4-way tap is actuatable by a wrench with a nominal width suitable for the sample bottle connection.

8. The device according to claim 7, wherein the wrench is only removable from the 4-way tap when in the first state.

9. A device for the emission-free sampling of volatile liquids, comprising: a 4-way tap having four lines and actuatable into two alternative states including a first state wherein a first and a second line are fluidly coupled and a third and a fourth line are fluidly coupled and a second state wherein the first and third lines are fluidly coupled and the second and fourth lines are fluidly coupled, wherein the first and second lines are fluidly connectable to a container holding the liquid to be tested, and the third and fourth lines are fluidly connectable to a sample bottle, a supply line for receiving an inert flushing medium and which is fluidly joined to the fourth line in a region of the connection to the sample bottle, and a discharge line for the inert flushing medium and which is branched from the third line in a region of the connection to the sample bottle and fluidly connectable to a disposal system, wherein the supply and discharge lines for the inert flushing medium are physically joined by a T or Y piece and comprise a coaxial double pipe up to the connection to the sample bottle, wherein the discharge line for the inert flushing medium is fitted with two spaced apart isolation elements, and an inspection glass located between the two isolation elements and wherein the volume enclosed by the double isolation is dimensioned such that when the 4-way tap is in the first state and the upstream isolation is opened, a predetermined filling of the sample bottle results.

10. The device according to claim 9, wherein the predetermined filling of the sample bottle is 60–95% of the total volume of the sample bottle.

* * * * *